US008866366B2

(12) United States Patent
Nakazawa et al.

(10) Patent No.: US 8,866,366 B2
(45) Date of Patent: Oct. 21, 2014

(54) PIEZOELECTRIC SENSOR DEVICE AND PIEZOELECTRIC SENSOR DEVICE DRIVE METHOD

(75) Inventors: Yusuke Nakazawa, Nagano (JP); Tomohide Onogi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 336 days.

(21) Appl. No.: 13/495,124

(22) Filed: Jun. 13, 2012

(65) Prior Publication Data

US 2012/0319529 A1  Dec. 20, 2012

(30) Foreign Application Priority Data

Jun. 15, 2011 (JP) ................................ 2011-132884

(51) Int. Cl.
| | |
|---|---|
| *H01L 41/107* | (2006.01) |
| *B06B 1/06* | (2006.01) |
| *H01L 41/04* | (2006.01) |
| *H01L 27/20* | (2006.01) |
| *H01L 41/113* | (2006.01) |
| *G01H 11/08* | (2006.01) |
| *A61B 8/00* | (2006.01) |

(52) U.S. Cl.
CPC ........... *H01L 41/1132* (2013.01); *A61B 8/4483* (2013.01); *B06B 1/06* (2013.01); *H01L 41/042* (2013.01); *H01L 27/20* (2013.01); *G01H 11/08* (2013.01)
USPC .......................................... 310/318; 310/319

(58) Field of Classification Search
CPC ... H01L 41/107; H01L 41/044; H01L 41/042; H01L 41/1132
USPC .................................................. 310/318, 319
See application file for complete search history.

(56) References Cited

U.S. PATENT DOCUMENTS

| | | | | |
|---|---|---|---|---|
| 5,138,217 | A  * | 8/1992 | Wada et al. ............... | 310/323.21 |
| 7,714,480 | B2 * | 5/2010 | Ohnishi et al. ................ | 310/324 |
| 2003/0094882 | A1* | 5/2003 | Mizuuchi ....................... | 310/317 |
| 2008/0034873 | A1 | 2/2008 | Habu et al. | |
| 2010/0043190 | A1* | 2/2010 | Habu et al. .................... | 29/25.35 |
| 2012/0212101 | A1* | 8/2012 | Tabata et al. .................. | 310/319 |

FOREIGN PATENT DOCUMENTS

| | | |
|---|---|---|
| JP | 2011-180403 A | 9/2011 |
| WO | WO-2008/018278 A1 | 2/2008 |

* cited by examiner

*Primary Examiner* — Derek Rosenau
*Assistant Examiner* — Bryan Gordon
(74) *Attorney, Agent, or Firm* — Global IP Counselors, LLP

(57) ABSTRACT

A piezoelectric sensor device includes a piezoelectric element, a signal processing unit, a polarization processing unit and a connection switching unit. The piezoelectric element has a piezoelectric body and a pair of electrodes sandwiching the piezoelectric body. The signal processing unit is configured to execute at least one of signal input from the piezoelectric element, and signal output to the piezoelectric element. The polarization processing unit is configured to execute polarization processing in which polarization voltage is applied to the piezoelectric element. The connection switching unit is configured to switch between a first connection state with which the electrodes and the signal processing unit are connected, and a second connection state with which the electrodes and the polarization processing unit are connected.

16 Claims, 4 Drawing Sheets

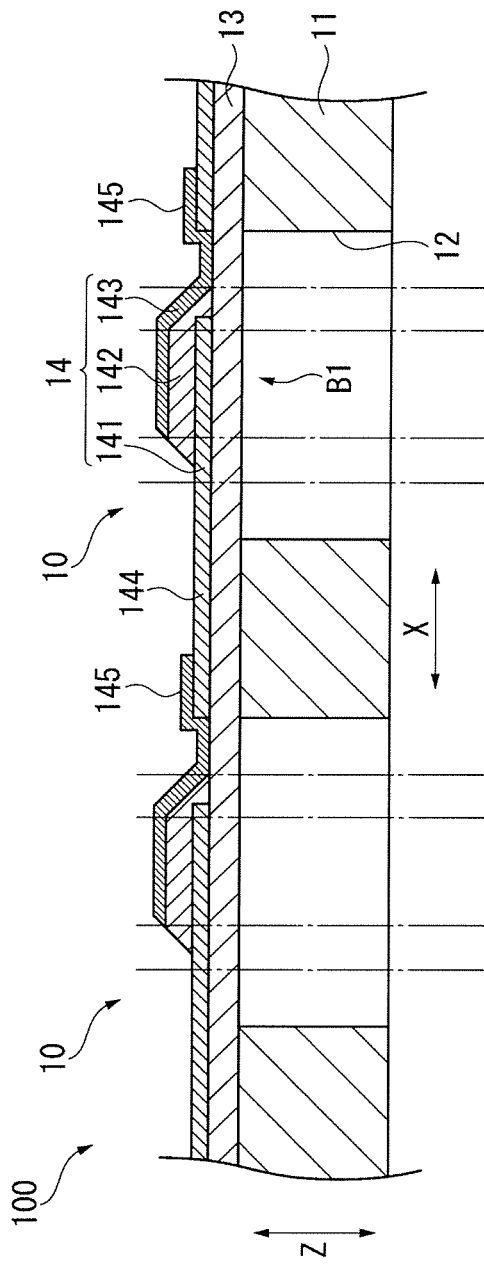
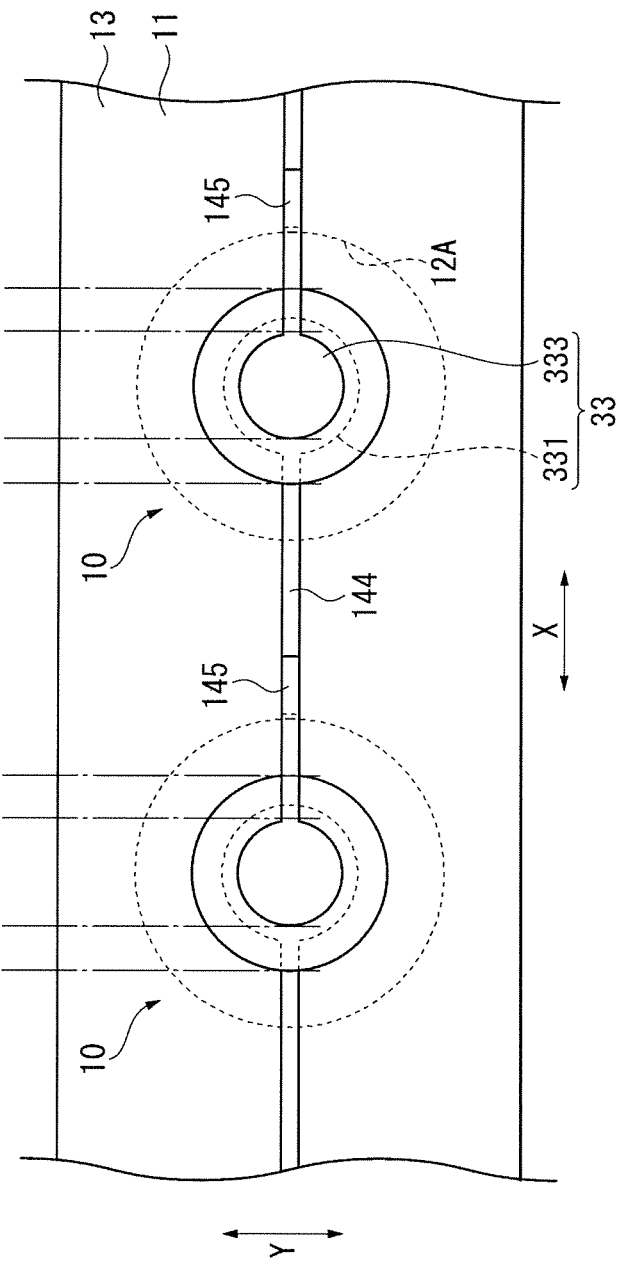
Fig. 2A
Fig. 2B

PIEZOELECTRIC SENSOR DEVICE AND PIEZOELECTRIC SENSOR DEVICE DRIVE METHOD

CROSS-REFERENCE TO RELATED APPLICATIONS

This application claims priority to Japanese Patent Application No. 2011-132884 filed on Jun. 15, 2011. The entire disclosure of Japanese Patent Application No. 2011-132884 is hereby incorporated herein by reference.

BACKGROUND

1. Technical Field

The present invention relates to a piezoelectric sensor device and a drive method for a piezoelectric sensor device.

2. Related Art

Piezoelectric sensor devices equipped with a piezoelectric body have been known from the past (e.g., see International Patent Publication No. 2008/018278).

The ultrasonic probe (piezoelectric sensor device) noted in the above mentioned publication has a configuration whereby a piezoelectric layer for transmitting, an electrode layer, and a piezoelectric layer for receiving are laminated in sequence. This kind of ultrasonic probe has the electrode layer formed on the piezoelectric layer for transmitting, and that piezoelectric layer for transmitting undergoes polarization processing. After that, the piezoelectric layer for receiving is laminated on the electrode layer, a peelable dielectric layer is further laminated on the piezoelectric layer for receiving, the piezoelectric layer for receiving undergoes polarization processing, the dielectric layer is peeled after polarization processing of that piezoelectric layer for receiving, thus producing the ultrasonic probe.

SUMMARY

However, with the ultrasonic probe noted in the above mentioned publication, polarization processing of the piezoelectric bodies (piezoelectric layer for transmitting and piezoelectric layer for receiving) is performed only during production, and after that, the dielectric layer for polarization processing is peeled.

However, with the effects of residual stress due to accumulated vibration, static electricity and the like on the piezoelectric body, there is the problem that its piezoelectric properties may degrade over time, so that the desired piezoelectric functions may not be obtained.

An object of the present invention is to provide a piezoelectric sensor device and a drive method of a piezoelectric sensor device capable of inhibiting the degradation over time of the piezoelectric body.

A piezoelectric sensor device according to one aspect of the present invention includes a piezoelectric element, a signal processing unit, a polarization processing unit and a connection switching unit. The piezoelectric element has a piezoelectric body and a pair of electrodes sandwiching the piezoelectric body. The signal processing unit is configured to execute at least one of detection processing for detecting an electrical signal output from the piezoelectric element, and drive processing for inputting a drive signal to the piezoelectric element to drive the piezoelectric element. The polarization processing unit is configured to execute polarization processing in which polarization voltage is applied to the piezoelectric element. The connection switching unit is configured to switch between a first connection state with which the electrodes and the signal processing unit are connected, and a second connection state with which the electrodes and the polarization processing unit are connected.

Note that as the piezoelectric element, it is possible to use a configuration for which driving is done by element single units, or to form element groups with a plurality of piezoelectric elements arranged in array form.

With the above described aspect of the present invention, the piezoelectric sensor device is equipped with a signal processing unit that executes at least one of signal input from the piezoelectric element, and signal output to the piezoelectric element, and a polarization processing unit for that executes polarization processing of the piezoelectric element piezoelectric body, and using a connection switching unit, the connection state between the piezoelectric element and the signal processing unit and polarization processing unit is switched. As a result, in the second connection state with which the piezoelectric element and the polarization processing unit are connected, it is possible to apply polarization voltage to the piezoelectric element, making it possible to perform polarization processing of the piezoelectric body. Therefore, even when there is degradation over time of the piezoelectric body piezoelectric properties due to the effects of residual stress, static electricity or the like, by executing the polarization processing noted above, it is possible to return the piezoelectric body piezoelectric properties to the pre-degradation state.

Also, when the connection switching unit is switched to the first connection state, the piezoelectric element and the signal processing unit are connected, so it is possible to perform at least one signal processing of detection processing and drive processing, making it possible to do normal driving of the piezoelectric sensor device.

Therefore, after switching the connection state of the connection switching unit to the second connection state and performing polarization processing of the piezoelectric body, by switching the connection state of the connection switching unit to the first connection state, it is possible to execute detection processing or drive processing using the piezoelectric body which underwent polarization processing, so it is possible to prevent a decrease in the performance of the piezoelectric sensor device.

The piezoelectric sensor device according to above described aspect of the present invention preferably further includes a controller configured to control switching of the switching state by the connection switching unit. The controller preferably includes a mode switching unit configured to switch between a signal processing mode in which signal processing by the signal processing unit is executed, and a calibration mode in which the polarization processing by the polarization processing unit is executed, and a connection controller configured to switch the connection switching unit to the first connection state when the mode switching unit switches to the signal processing mode, and to switch the connection switching unit to the second connection state when the mode switching unit switches to the calibration mode.

With the above described aspect of the present invention, when switched to the calibration mode by the mode switching unit, the connection controller switches the connection switching unit to the second connection state. Also, after applying polarization voltage to the piezoelectric element and executing polarization processing of the piezoelectric body or the like, when switched to the signal processing mode by the mode switching unit, the connection controller switches the connection switching unit to the first connection state, and the concerned piezoelectric sensor device is in a state for which it is possible to have signal processing executed by the signal processing unit. Therefore, since the connection switching unit is automatically controlled by the controller, the user does not need to be conscious of the connection state of the connection switching unit, making it possible to easily execute polarization processing of the piezoelectric body.

The piezoelectric sensor device of the above described aspect the present invention preferably further includes a power switch configured to switch to a power supplied state with which power is supplied to the piezoelectric sensor device, and a power unsupplied state with which supply of the power to the piezoelectric sensor device is shut off. The mode switching unit is preferably configured to switch to the calibration mode when the power switch is switched to the power supplied state, and to switch to the signal processing mode when the polarization processing by the polarization processing unit ends.

With the above described aspect of the present invention, each time the piezoelectric sensor device power switch is switched to the power supplied state, the mode switching unit switches to the calibration mode. Therefore, when the power is turned on to the piezoelectric sensor device, there is always application of polarization voltage to the piezoelectric element so that polarization processing of the piezoelectric body is executed, so when switched to the signal processing mode by the mode switching unit, it is possible to execute signal processing using the piezoelectric element having a piezoelectric body that has undergone polarization processing. Specifically, when executing detection processing using the piezoelectric element, it is possible to improve the detection sensitivity with the piezoelectric element, and when executing drive processing using the piezoelectric element, it is possible to drive the piezoelectric element with the desired drive volume according to the drive signal.

With the piezoelectric sensor device of the above described aspect of the present invention, the controller preferably includes a signal acquisition unit configured to acquire an input signal indicative of signal processing to be executed by the signal processing unit, and the mode switching unit is preferably configured to switch to the calibration mode when the signal acquisition unit acquires the input signal, and to switch to the signal processing mode when the polarization processing by the polarization processing unit ends.

Here, the signal acquisition unit acquires the input signal input from an operating unit operable by a user, or the input signal input from an external control device or the like, and as a trigger for this input signal, the signal processing unit executes detection processing or drive processing of the piezoelectric element.

With the above described aspect of the present invention, each time an input signal is acquired, specifically, before signal processing is executed by the signal processing unit, polarization processing of the piezoelectric body is executed. Because of this, at the time of signal processing by the signal processing unit, it is possible to reliably execute signal processing using the piezoelectric element having a piezoelectric body that has undergone polarization processing, making it possible to further improve the precision of the signal processing.

With the piezoelectric sensor device of the above described aspect of the present invention, the controller preferably includes a signal acquisition unit configured to acquire an input signal indicative of signal processing to be executed by the signal processing unit, and a clock unit configured to measure an elapsed time from a processing stop point when the signal processing by the signal processing unit ended. The mode switching unit is preferably configured to switch to the calibration mode when the input signal was not acquired by the signal acquisition unit during a prescribed standby transition period from the processing stop point, and to switch to the signal processing mode when the polarization processing by the polarization processing unit ends.

With the above described aspect of the present invention, when a signal processing sequence by the signal processing unit ends, and the piezoelectric sensor device is in a standby state, polarization processing is executed by the polarization processing unit. With such a configuration, polarization processing is not executed while the signal processing sequence is being executed, so it is possible to execute rapid signal processing without the signal processing being interrupted by the polarization processing. Also, because polarization processing is executed when in a standby state, when next executing signal processing, the piezoelectric element piezoelectric body is in a state having undergone polarization processing, making it possible to prevent a decrease in the precision with the signal processing.

A piezoelectric sensor device drive method according to another aspect of the present invention is a method for driving a piezoelectric sensor device including a piezoelectric element having a piezoelectric body and a pair of electrodes sandwiching the piezoelectric body, a signal processing unit configured to execute at least one of detection processing for detecting an electrical signal output from the piezoelectric element and drive processing for inputting a drive signal to the piezoelectric element to drive the piezoelectric element, a polarization processing unit configured to execute polarization processing in which polarization voltage is applied to the piezoelectric element, and a connection switching unit configured to switch between a first connection state with which the electrodes and the signal processing unit are connected and a second connection state with which the electrodes and the polarization processing unit are connected. The piezoelectric sensor device drive method includes: switching a connection state of the connection switching unit to the second connection state, and applying the polarization voltage to the piezoelectric element using the polarization processing unit; and after the switching of the connection state to the second connection state, switching the connection state of the connection switching unit to the first connection state, and executing the at least one of the detection processing and the signal processing by the signal processing unit.

With the above described aspect of the present invention, it is possible to exhibit the same operating effect as the previously described piezoelectric sensor device. Specifically, the piezoelectric sensor device is equipped with a signal processing unit for executing at least one of signal input from the piezoelectric element, and signal output to the piezoelectric element, and a polarization processing unit for executing polarization processing of the piezoelectric element piezoelectric body, and the connection state between the piezoelectric element and the signal processing unit and the polarization processing unit is switched by the connection switching unit. As a result, in the second state with which the piezoelectric element and the polarization processing unit are connected, it is possible to apply a polarization voltage to the piezoelectric element, making it possible to perform polarization processing of the piezoelectric body. Therefore, even when there is degradation over time of the piezoelectric body piezoelectric properties due to the effect of residual stress, static electricity or the like, by executing the polarization processing noted above, it is possible to return the piezoelectric body piezoelectric properties to the pre-degradation state.

Also, when the connection switching unit is switched to the first connection state, the piezoelectric element and the signal processing unit are connected, so it is possible to perform at least one of detection processing and drive processing, and it is possible to do normal driving of the piezoelectric sensor device.

Then, after the connection state of the connection switching unit is switched to the second connection state and polarization processing of the piezoelectric body is performed, the connection state of the connection switching unit is switched to the first connection state, so detection processing or drive processing is executed using the piezoelectric element having the piezoelectric body which has undergone polarization processing, making it possible to prevent a decrease in performance of the piezoelectric sensor device.

BRIEF DESCRIPTION OF THE DRAWINGS

Referring now to the attached drawings which form a part of this original disclosure:

FIGS. 2A and 2B are diagrams showing the configuration of the receiving element of the embodiment.

DETAILED DESCRIPTION OF EXEMPLARY EMBODIMENTS

Figure 1:
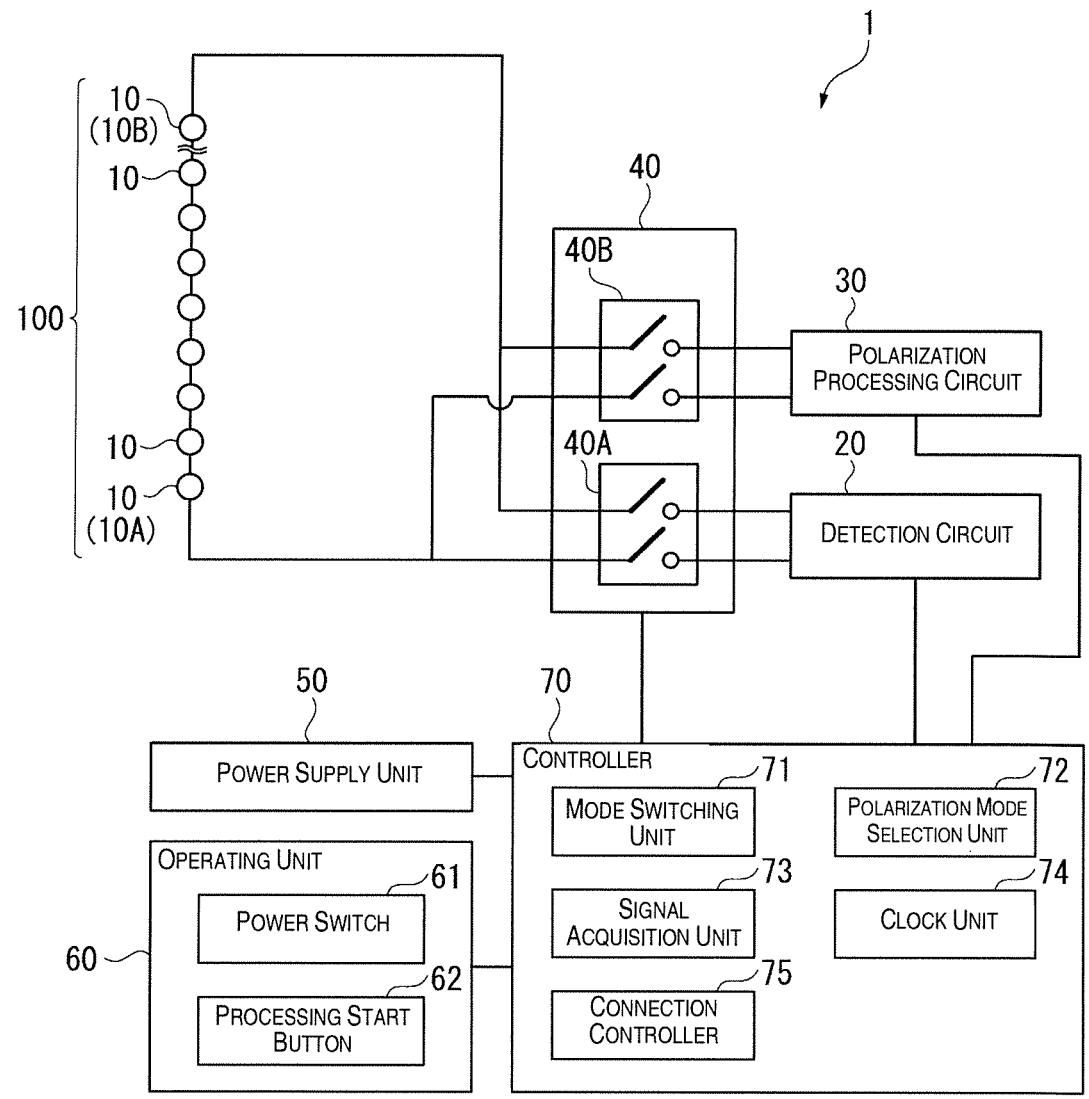
FIG. 1 is a diagram showing the configuration of the ultrasonic sensor of an embodiment of the present invention.

Following, we will describe an embodiment of the present invention while referring to the drawings.

Schematic Configuration of Ultrasonic Sensor

FIG. 1 is a diagram showing the configuration of an ultrasonic sensor 1 as the piezoelectric sensor device. This ultrasonic sensor 1 is a sensor for detecting the distance between the ultrasonic sensor 1 and the object to be detected as well as the state of the object to be detected by receiving ultrasonic waves reflected by the object to be detected that were sent to the object to be detected. This kind of ultrasonic sensor 1 can be used for various kinds of devices that send or receive ultrasonic waves, such as a biopsy device for measuring in vivo blood vessel position, blood flow speed, blood pressure and the like, for example, by sending and receiving ultrasonic waves, a stress measuring device for measuring pressing force or sheer force acting on an elastic film by detecting through use of ultrasonic waves the movement of the elastic film provided on the surface to the ultrasonic sensor 1, an ultrasonic cleaning device that uses ultrasonic waves to measure the distance from a target object and cleans that target object with sound pressure according to the measured distance, or the like.

As shown in FIG. 1, this ultrasonic sensor 1 is equipped with a plurality of receiving elements 10 (piezoelectric elements), a detection circuit 20 (signal processing unit) for detecting detection signals output from the receiving element 10, a polarization processing circuit 30 (polarization processing unit), a connection switching circuit 40 (connection switching unit), a power supply unit 50, an operating unit 60, and a controller 70.

Configuration of Receiving Element

FIGS. 2A and 2B are diagrams showing the schematic configuration of the receiving element 10. In specific terms, FIG. 2A is a cross section view of the receiving element 10, and FIG. 2B is a plan view of the receiving element 10.

The receiving element 10 is an element that receives ultrasonic waves and converts them to electrical signals.

A plurality of these receiving elements 10 are arranged at equal intervals on a support unit 11 along the axial directions of the respective X axis and Y axis which are orthogonal to each other, and a receiving element group 100 with an array configuration is constituted by this plurality of receiving elements 10.

As shown in FIGS. 2A and 2B, each receiving element 10 is equipped with a support unit 11 on which an opening 12 is formed, a support film 13 which covers the support unit 11 and blocks the opening 12, and a laminated body 14 formed on the support film 13.

The opening 12 formed on the support unit 11 is formed, for example, in the circular shape seen with the plan view as shown in FIG. 2B. As a result, at a diaphragm 131 which is the support film 13 on the inside of the opening 12, it is possible to make the stress in relation to the deflection of the diaphragm 131 uniform.

Film formation of the support film 13 is done on the support unit 11 in a state with the opening 12 blocked. This support film 13 is constituted using a two-layer constitution of an $SiO_2$ layer and a $ZrO_2$ layer, for example. Here, when the support unit 11 is an Si substrate, film formation of the $SiO_2$ layer can be done by doing thermal oxidation processing of the substrate surface. Also, film formation of the $ZrO_2$ layer can be done using a method such as sputtering or the like on the $SiO_2$ layer, for example. Here, the $ZrO_2$ layer is a layer for preventing diffusion of Pb, which constitutes PZT, into the $SiO_2$ layer when using PZT as the piezoelectric film 142 described later, for example. The $ZrO_2$ layer also has effects such as increasing the deflection efficiency in relation to distortion of the piezoelectric film 142.

The laminated body 14 is equipped with a lower electrode 141 laminated on the top layer of the support film 13, a piezoelectric film 142 as the piezoelectric body formed on the lower electrode 141, and an upper electrode 143 formed on the piezoelectric film 142. In other words, the laminated body 14 has a constitution with which the piezoelectric film 142 is sandwiched by a pair of electrodes (lower electrode 141 and upper electrode 143).

Also, as shown in FIGS. 2A and 2B, on the lower electrode 141, a lower electrode wire 144 is drawn along the support film 13. Also, on the upper electrode 143, an upper electrode wire 145 is drawn facing opposite the drawing direction of the lower electrode wire 144 along the support film 13. Then, with a planar view, the lower electrode wire 144 is overlapping the upper electrode wire 145 of the receiving element 10 that is arranged adjacently. In this way, the receiving elements 10 are serially connected as shown in FIG. 1 by having the lower electrode wire 144 and the upper electrode wire 145 of each receiving element 10 overlap for connection.

With this kind of receiving element group 100, by a plurality of receiving elements 10 being serially connected, the detection signals output from the receiving elements 10 are added together, so it is possible to output detection signals with a large signal value to the detection circuit 20.

Though not shown in detail, with this embodiment, we showed an example of a sensor configuration whereby, of the receiving element groups 100, only the element groups arranged in the X axis direction are connected serially to constitute the receiving element group 100, such receiving element groups 100 are provided in parallel along the Y axis, and each of the receiving element groups 100 are connected individually to the detection circuit 20, but the invention is not restricted thereto. For example, by the receiving elements 10 arranged at one end in the X axis direction being serially connected with the receiving elements 10 adjacent in the Y axis direction, it is also possible to have a configuration for which the receiving elements 10 arranged in the X axis direction and the Y axis direction are serially connected.

The piezoelectric film 142 is formed by doing film formation of, for example, PZT (lead zirconate titanate) in film form. With this embodiment, PZT is used as the piezoelectric film 142, but any material can be used as long as it is a material that can be contracted in the inner surface direction by applying voltage, for example lead titanate ($PbTiO_3$), lead zirconate ($PbZrO_3$), lead lanthanum titanate ($(Pb, La)TiO_3$) or the like may also be used.

With such a receiving element 10, by ultrasonic waves being received at the diaphragm 131, the diaphragm 131 vibrates in the film thickness direction (Z axis direction in FIG. 2A). As a result, potential difference is generated at the surface of the lower electrode 141 side and the surface of the upper electrode 143 side of the piezoelectric film 142, and a detection signal (current) is output from the upper electrode 143 and the lower electrode 141 according to the displacement volume of the piezoelectric film 142.

Configuration of Detection Circuit

The detection circuit 20 shown in FIG. 1 is a circuit that executes detection processing for detecting (acquiring) detection signals output from each receiving element 10, and is connected to the previously described receiving element group 100 via the connection switching circuit 40. More specifically, the detection circuit 20 is connected to the lower electrode wire 144 of the receiving elements 10 (receiving elements 10A) arranged at one end of the receiving element group 100 and to the upper electrode wire 145 of the receiving elements 10 (receiving element 10B) arranged at the other end of the receiving element group 100. Then, this detection circuit 20 amplifies the voltage value of the detection signal input from the receiving element group 100 and outputs it to the controller 70.

Configuration of Polarization Processing Circuit

The polarization processing circuit 30 is equipped with a voltage source capable of outputting a polarization voltage for performing polarization processing on the previously described receiving elements 10, and is connected to the receiving element group 100 via the connection switching circuit 40. By this polarization processing circuit 30 applying the polarization voltage to the receiving element group 100, divided voltage of the concerned polarization voltage is applied between the lower electrode 141 and the upper electrode 143 of each receiving element 10.

As a result, polarization processing is executed for which the direction of the polarizers of the piezoelectric film 142 between the lower electrode 141 and the upper electrode 143 are aligned in one direction. Note that the applied voltage and time may be executed at preset values according to the characteristics of the piezoelectric film 142, for example.

Configuration of Connection Switching Circuit

The connection switching circuit 40 is constituted using a switching element such as a (TFT (Thin Film Transistor)) or the like, for example, and is equipped with a first switch unit 40A provided between the receiving element group 100 and the detection circuit 20, and a second switch unit 40B provided between the receiving element group 100 and the polarization processing circuit 30. Then, the first switch unit 40A switches the connection state of the receiving element group 100 and the detection circuit 20 by the control of the controller 70. Also, the second switch unit 40B switches the connection state of the receiving element group 100 and the polarization processing circuit 30 by the control of the controller 70.

Here, a state with the receiving element group 100 and the detection circuit 20 connected by the first switch unit 40A, and the receiving element group 100 and the polarization processing circuit 30 disconnected by the second switch unit 40B is the first connection state of the present invention. Also, a state with the receiving element group 100 and the detection circuit 20 disconnected by the first switch unit 40A, and the receiving element group 100 and the polarization processing circuit 30 connected by the second switch unit 40B is the second connection state of the present invention.

Configuration of Power Supply Unit

The power supply unit 50 supplies power to the ultrasonic sensor 1. As this power supply unit 50, for example, it is possible to supply power to the ultrasonic sensor 1 by connecting to a power source such as an outlet or the like, or using a battery, power generating unit or the like.

Configuration of Operating Unit

The operating unit 60 is provided on an external part of the ultrasonic sensor 1 that is not shown, and is a part with which input signals are input by the operation of a user. As this operating unit 60, for example, equipped are a power switch 61 that activates the ultrasonic sensor 1 by power from the power supply unit 50, a processing start button 62 that executes receiving processing (transmission and receiving processing) of ultrasonic waves, a polarization selection unit (not shown) for setting the timing of the polarization processing or the like.

Configuration of Controller

The controller 70 is connected to the previously described detection circuit 20, the polarization processing circuit 30, the connection switching circuit 40, the power supply unit 50, and the operating unit 60.

This controller 70 is constituted from an integrated circuit such as an IC (Integrated Circuit) or the like for example, and does overall control of the ultrasonic sensor 1. In specific terms, as shown in FIG. 1, the controller 70 is constituted equipped with a mode switching unit 71, a polarization mode selection unit 72, a signal acquisition unit 73, a clock unit 74, a connection controller 75 and the like.

The mode switching unit 71 switches and sets the operating mode of the ultrasonic sensor 1. In specific terms, the mode switching unit 71 switches between the signal processing mode which allows detection by the detection circuit 20 of detection signals from the receiving element group 100, and the calibration mode for which polarization processing of the receiving element group 100 is executed by the polarization processing circuit 30.

Note that this mode switching unit 71 is normally set to the signal processing mode. Then, it is set to the calibration mode as appropriate according to the polarization timing selected using the polarization mode selection unit 72 described later.

When switched to the calibration mode by the mode switching unit 71, the polarization mode selection unit 72 selects at which timing to have polarization processing done by the polarization processing circuit 30. In specific terms, the polarization mode selection unit 72 sets the polarization timing by the polarization selection unit which is provided on the previously described operating unit 60 being operated by a user.

Here, polarization timings that can be selected include power-on timing, each-receive timing, standby-transition timing, and the like.

The power-on timing is the timing at which the power from the power supply unit 50 is supplied when the power switch 61 is set to an on state. Specifically, when power-on timing is selected using the polarization mode selection unit 72, the mode switching unit 71 switches the operating mode to the calibration mode each time the power switch 61 goes to an on state, and when the polarization processing ends, it switches to the signal processing mode.

Also, each-receive timing is the timing by which input signals to the effect of executing detection processing are input from the operating unit 60. Specifically, when each-receive timing is selected using the polarization mode selection unit 72, the mode switching unit 71 switches the operating mode to the calibration mode each time before detection processing is executed by the detection circuit 20, and switches to the signal processing mode when the polarization processing ends.

Also, the standby-transition timing is the timing at which a prescribed standby-transition time has elapsed after detection processing of the ultrasonic waves has ended. Specifically, when the standby-transition timing is selected using the polarization mode selection unit 72, the mode switching unit 71 switches the operating mode to the calibration mode after detection processing has been executed by the detection circuit 20, and a prescribed standby-transition time has elapsed without detection processing being executed, and switches to the signal processing mode when polarization processing ends.

The signal acquisition unit 73 acquires the input signals input from the operating unit 60. As described above, examples of this input signal include input signals indicating that the power switch 61 has been switched to an on state, an input signal to the effect that the processing start button 62 has been turned on, in other words, to the effect that detection processing of ultrasonic waves by the receiving element group 100 has started, input signals to the effect that polarization timing has been selected, and the like.

The clock unit 74 is equipped with a timer for measuring time. Also, the clock unit 74 measures the elapsed time since detection processing was executed by the detection circuit 20 using this timer.

The connection controller 75 sets the connection switching circuit 40 state as appropriate according to the operating mode set by the mode switching unit 71.

Specifically, the connection controller 75 switches the connection switching circuit 40 to the first connection state when the signal processing mode is set by the mode switching unit 71. The connection controller 75 also switches the connection switching circuit 40 to the second connection state when the calibration mode is set by the mode switching unit 71.

Configuration of Ultrasonic Sensor

Figure 3:
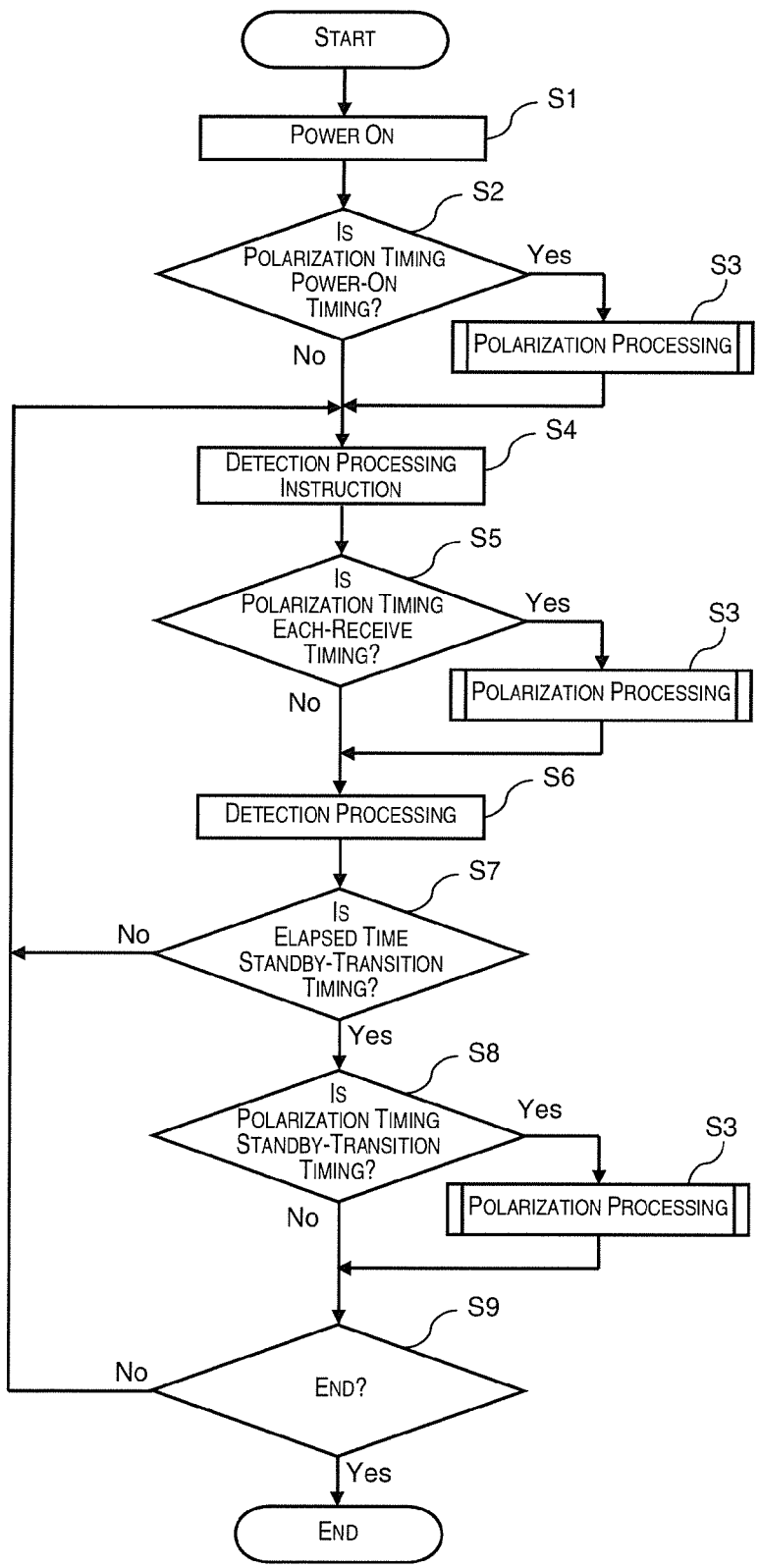
FIG. 3 is a flow chart showing the operation of the ultrasonic sensor of the embodiment.

FIG. 3 is a flow chart showing the operation of the ultrasonic sensor 1.

When the power switch 61 is turned on, the signal acquisition unit 73 acquires input signals to that effect from the operating unit 60, and outputs the results to the mode switching unit 71 (step S1).

The mode switching unit 71 which receives these results determines whether the power-on timing is set as the polarization timing by the polarization mode selection unit 72 (step S2).

At step S2, when it is determined that the power-on timing (drawing needs to be revised) is set as the polarization timing, the mode switching unit 71 switches the operating mode of the ultrasonic sensor 1 to the calibration mode. As a result, the polarization processing described hereafter is performed (step S3).

Figure 4:
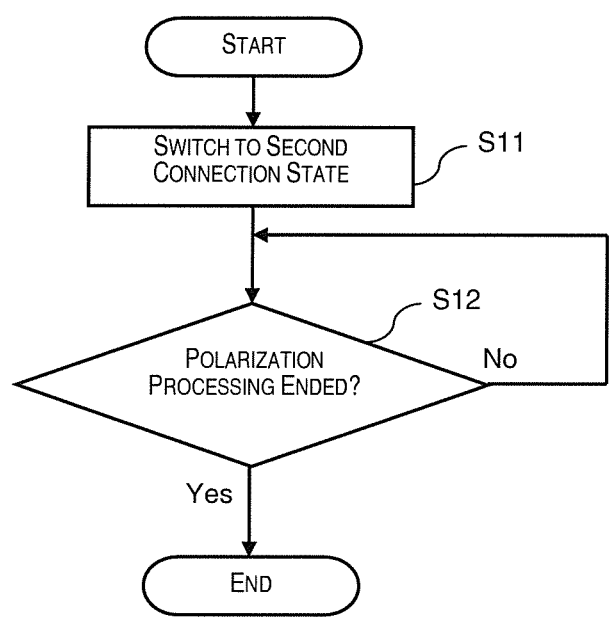
FIG. 4 is a flow chart of the polarization processing of the embodiment.

FIG. 4 is a flow chart of the polarization processing.

When the polarization processing starts, the connection controller 75 switches the connection state of the connection switching circuit 40 to the second connection state (step S11). As a result, polarization voltage is applied between the lower electrode 141 and the upper electrode 143 of each receiving element 10 from the polarization processing circuit 30, and polarization processing of the piezoelectric film 142 is performed.

Next, the connection controller 75 determines whether the polarization processing of the piezoelectric film 142 has ended (step S12). This determination can be performed by timing the processing time with the timer, for example.

When it is determined at step S12 that the polarization processing has not ended, the connection controller 75 maintains the second connection state, and executes the polarization processing until the polarization processing of each piezoelectric film 142 has ended.

When it is determined at step S12 that the polarization processing has ended, then polarization processing ends.

When the polarization processing of this step S3 ends, or at the previously described step S2, it is determined that power-on timing is not set as the polarization timing, the mode switching unit 71 switches the operating mode of the ultrasonic sensor 1 to the signal processing mode, and as a result, the connection controller 75 switches the connection state of the connection switching circuit 40 to the first connection state.

Then, when the processing start button 62 is turned on with the operating unit 60, the signal acquisition unit 73 acquires input signals to that effect, and outputs the results to the connection controller 75 (step S4).

The connection controller 75 which receives these results determines whether or not the each-receive timing is set as the polarization timing by the polarization mode selection unit 72 (step S5).

At step S5, when it is determined that each-receive timing is set as the polarization timing, the polarization processing of the previously described step S3 is performed.

When the polarization processing of this step S3 ends, or when it is determined at the previously described step S5 that each-receive timing is not set as the polarization timing, the connection controller 75 switches the connection state of the connection switching circuit 40 to the first connection state. As a result, as described hereafter, the detection processing by the detection circuit 20 is executed (step S6).

At this step S6, ultrasonic waves are issued from an ultrasonic wave transmitting element (not shown), and the ultrasonic waves reflected by the object to be detected are received by each receiving element 10.

With the receiving elements 10, by receiving ultrasonic waves at the diaphragm 131 (passive film), the diaphragm 131 vibrates in the film thickness direction, and electrical signals (detection signals) are output from the piezoelectric film 142 deformed by the vibration to the detection circuit 20 via the lower electrode 141 and upper electrode 143. The detection circuit 20 amplifies the voltage value of this detection signal and outputs it to the controller 70.

Then the controller 70 processes the detection signals output from the detection circuit 20. In specific terms, with the controller 70, the time from the transmission timing when the ultrasonic waves are transmitted from the ultrasonic wave transmitting element until the detection signal receive timing is calculated, for example the distance from the ultrasonic sensor 1 to the object to be detected or the like is calculated, and this is output as measurement results to an output device or the like (not shown).

Then, when this detection processing is stopped by the processing start button 62 being turned off or the like, the clock unit 74 times the elapsed time from the point that the detection processing stopped, and the connection controller 75 determines whether the standby-transition time has elapsed or not (step S7).

At step S7, when it is determined that the standby-transition time has not elapsed, the process returns to the processing of step S4, and waits until the processing start button 62 is turned on.

At step S7, when it is determined that the standby-transition time has elapsed, the connection controller 75 determines whether or not the standby-transition timing is set as the polarizing timing by the polarization mode selection unit 72 (step S8).

At step S8, when it is determined that the standby-transition timing is set as the polarization timing, the previously described polarization processing of step S3 is performed.

At step S8, when it is determined that the standby-transition timing is not set as the polarization timing, it is determined whether or not ending of the operation of the ultrasonic sensor 1 (power switch 61 off) has been instructed (step S9).

Then, at step S9, when it is determined that ending has not been instructed, the process returns to the processing of step S4, and waits for the processing start button 62 to be turned on again.

On the other hand, at step S9, when it is determined that ending has been instructed, operation of the ultrasonic sensor 1 is stopped.

With the ultrasonic sensor 1 of the embodiment described above, the following effects are exhibited.

The ultrasonic sensor 1 is equipped with a receiving element group 100 constituted by a plurality of receiving elements 10, a detection circuit 20 for detecting detection signals output from the receiving element group 100, a polarization processing circuit 30 for doing polarization processing of each receiving element 10 of the receiving element group 100, and a connection switching circuit 40 for switching the connection state of the receiving element group 100 and the detection circuit 20, and the connection state of the receiving element group 100 and the polarization processing circuit 30.

This kind of ultrasonic sensor 1 is able to apply polarization voltage to each receiving element 10 in the second connection state with which the receiving element group 100 and the polarization processing circuit 30 are connected, making it possible to perform polarization processing of the piezoelectric film 142. Therefore, even when there is degradation over time of the polarization properties of the piezoelectric film 142 due to the effect of residual stress and static electricity and the like, by executing polarization processing, it is possible to orient the polarization direction of the piezoelectric film 142 in one direction, and possible to return the polarization properties to the pre-degradation state.

Also when the connection switching circuit 40 is switched to the first connection state, the receiving element group 100 and the detection circuit 20 are connected, so it is possible to perform detection processing, and possible to do normal driving of the ultrasonic sensor 1.

Therefore, when the connection state of the connection switching circuit 40 is switched to the second connection state, after polarization processing of the piezoelectric film 142 of each receiving element 10 is performed, by switching the connection state of the connection switching circuit 40 to the first connection state, it is possible to execute detection processing using a piezoelectric film 142 (receiving element 10) which has undergone polarization processing, so it is possible to prevent a decrease in the performance of the ultrasonic sensor 1.

Also, the controller 70 of the ultrasonic sensor 1 is equipped with a mode switching unit 71 that switches between the signal processing mode and the calibration mode. Then, by switching to the calibration mode using the mode switching unit 71, the connection controller 75 switches the connection switching circuit 40 to the second connection state. Also, when switched to the signal processing mode by the mode switching unit 71, the connection controller 75 switches the connection switching circuit 40 to the first connection state, and the ultrasonic sensor 1 is in a state for which detection processing by the detection circuit 20 can be executed. Therefore, since the connection switching circuit 40 is automatically controlled by the controller 70, the user does not need to be conscious of the connection state of the connection switching circuit 40, making it possible to easily execute polarization processing of the receiving element group 100 (piezoelectric film 142 of each receiving element 10).

Furthermore, the controller 70 of the ultrasonic sensor 1 is equipped with a polarization mode selection unit 72, and the mode switching unit 71 switches from the signal processing mode to the calibration mode by the polarization timing set using the polarization mode selection unit 72.

Then, when the power-on timing is set using the polarization mode selection unit 72, each time the power switch 61 is turned on, the mode switching unit 71 switches to the calibration mode. Because of this, when the power is turned on for the ultrasonic sensor 1, polarization processing of the receiving element group 100 is always executed, so when the concerned ultrasonic sensor 1 is activated, each receiving element 10 is always in a polarized state, and it is possible to increase the detection sensitivity of the receiving element group 100. Also, since the timing of the execution of the polarization processing is only when the power turned on, polarization processing is executed during detection processing of detection signals by the detection circuit 20, and it is possible to execute detection processing rapidly without interrupting processing.

Also, when each-receive timing is set by the polarization mode selection unit 72, each time an input signal to the effect that detection processing has started is acquired, specifically, each time before detection processing is executed by the detection circuit 20, the polarization processing of the receiving element group 100 is executed. Because of this, during detection processing by the detection circuit 20, it is possible to execute detection processing using the receiving element group 100 which has reliably undergone polarization processing, so it is possible to further improve the precision of the detection processing.

Furthermore, when standby-transition timing is set using the polarization mode selection unit 72, when the detection processing sequence by the detection circuit 20 has ended, and the ultrasonic sensor 1 goes to a standby state, polarization processing is executed by the polarization processing circuit 30. With this kind of configuration, polarization processing is not executed during execution of the detection processing sequence, so it is possible to execute rapid detection processing without interruption of the detection processing by the polarization processing. Also, since polarization processing is frequently executed from the power-on timing, it is possible to increase the precision of the detection processing.

Here, compared to an ultrasonic sensor constituted by a single element (one receiving element), an ultrasonic sensor constituted with a plurality of receiving elements serially connected has a tendency to have lower receiving sensitivity. However, with the ultrasonic sensor 1 of this embodiment, even when a plurality of receiving elements 10 are serially connected to constitute the receiving element group 100, by doing polarization processing of the piezoelectric film 142 and aligning the polarization state, it is possible to prevent a decrease in the receiving sensitivity.

Furthermore, the laminated body 14 of each receiving element 10 is constituted by a thin film type piezoelectric film 142 and the lower electrode 141 and upper electrode 143, so compared to when doing polarization processing of a bulk type piezoelectric element, it is possible to perform polarization processing by applying a lower voltage.

Modified Embodiments

The present invention is not restricted to the embodiment described above, and variations and improvements within a scope that can accomplish the object of the present invention are included within the invention.

With the embodiment described above, an example was shown of a configuration for which the three settings could be set for the polarization timing, including power-on timing, each-receive timing, and standby-transition timing, but a configuration that allows any one or more to be set is acceptable. Also, the polarization timing is not restricted to the timings shown in the example. For example, the polarization timing may also be the timing when the power switch 61 is turned off, and may be one out of every few receive timings rather than each-receive timing, or the like.

Furthermore, it is also possible to use periodic timing such as once every three days or the like, and it is also possible to provide a switch for performing polarization processing on the operating unit 60, and to use the timing indicated as desired by the user using that switch.

With the embodiment described above, an example was shown of a configuration for which the connection switching circuit 40 is controlled by the controller 70 to switch between the first connection state and the second connection state, but the invention is not restricted to this, and a configuration may also be used for which the connection switching circuit is constituted using a manual switch or the like, and the user switches the connection manually.

With the embodiment described above, an example was shown of a configuration for which ultrasonic waves are received by equipping the detection circuit 20 for detecting electrical signals output from the piezoelectric film 142 as the signal processing unit, but the invention is not restricted to this, and as the signal processing unit, it is also possible to adopt a configuration with which drive signals are input to the receiving elements 10 and drive processing is executed by driving the receiving elements 10 as the transmitting element. Specifically, a configuration may be adopted with which voltage is applied between the lower electrode 141 and the upper electrode 143 by inputting drive signals, and ultrasonic waves are transmitted by vibrating the piezoelectric film 142. It is also possible to use a configuration for which the signal processing unit performs both receiving and transmitting. Furthermore, it is also possible to have an ultrasonic sensor which performs both detection processing and drive processing using the present invention.

With the embodiment described above, an example was shown of a configuration for which a plurality of receiving elements 10 are serially connected, but it is also possible to have a single count (single element) for the number of receiving elements 10, for example it is also possible to use a configuration for which a plurality of the receiving elements 10 are connected in parallel so as to be a configuration applied in cases such as the previously described configuration of transmitting ultrasonic waves.

With the embodiment described above, described as the piezoelectric element was a receiving element 10 equipped with thin film type piezoelectric film 142 and a laminated body 14 constituted by the lower electrode 141 and the upper electrode 143, but the piezoelectric element may also be a bulk type.

With the embodiment described above, an example was shown of a configuration for which polarization processing of the piezoelectric film 142 is performed, and detection by the detection circuit 20 is performed after the polarization processing, but it is also possible to use a configuration with which after polarization processing, based on the detection results of the concerned detection circuit 20 or the like, the usability status of the piezoelectric film 142 is determined, and processing is performed according to the determination results.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A piezoelectric sensor device comprising:
   a piezoelectric element having a piezoelectric body and a pair of electrodes sandwiching the piezoelectric body;
   a signal processing unit configured to execute at least one of signal input from the piezoelectric element, and signal output to the piezoelectric element;
   a polarization processing unit configured to execute polarization processing in which polarization voltage is applied to the piezoelectric element; and
   a connection switching unit configured to switch between a first connection state with which the electrodes and the signal processing unit are connected, and a second connection state with which the electrodes and the polarization processing unit are connected.

2. The piezoelectric sensor device according to claim 1, wherein
   the signal input from the piezoelectric element includes detection processing for detecting an electrical signal output from the piezoelectric element.

3. The piezoelectric sensor device according to claim 2, wherein
   the signal output to the piezoelectric element includes drive processing for outputting a drive signal to the piezoelectric element to drive the piezoelectric element.

4. The piezoelectric sensor device according to claim 1, wherein
   the signal output to the piezoelectric element includes drive processing for outputting a drive signal to the piezoelectric element to drive the piezoelectric element.

5. The piezoelectric sensor device according to claim 1, further comprising
   a controller configured to control switching of the switching state by the connection switching unit, the controller including
      a mode switching unit configured to switch between a signal processing mode in which signal processing by the signal processing unit is executed, and a calibration mode in which the polarization processing by the polarization processing unit is executed, and
      a connection controller configured to switch the connection switching unit to the first connection state when the mode switching unit switches to the signal processing mode, and to switch the connection switching unit to the second connection state when the mode switching unit switches to the calibration mode.

6. The piezoelectric sensor device according to claim 5, further comprising
   a power switch configured to switch to a power supplied state with which power is supplied to the piezoelectric sensor device, and a power unsupplied state with which supply of the power to the piezoelectric sensor device is shut off,
   the mode switching unit being configured to switch to the calibration mode when the power switch is switched to the power supplied state, and to switch to the signal processing mode when the polarization processing by the polarization processing unit ends.

7. The piezoelectric sensor device according to claim 5, wherein
   the controller includes a signal acquisition unit configured to acquire an input signal indicative of signal processing to be executed by the signal processing unit, and
   the mode switching unit is configured to switch to the calibration mode when the signal acquisition unit acquires the input signal, and to switch to the signal processing mode when the polarization processing by the polarization processing unit ends.

8. The piezoelectric sensor device according to claim 5, wherein
   the controller includes
      a signal acquisition unit configured to acquire an input signal indicative of signal processing to be executed by the signal processing unit, and
      a clock unit configured to measure an elapsed time from a processing stop point when the signal processing by the signal processing unit ended, and
   the mode switching unit is configured to switch to the calibration mode when the input signal was not acquired by the signal acquisition unit during a prescribed standby transition period from the processing stop point, and to switch to the signal processing mode when the polarization processing by the polarization processing unit ends.

9. A piezoelectric sensor device comprising:
   a piezoelectric element having a piezoelectric body and a pair of electrodes sandwiching the piezoelectric body;
   a signal processing unit configured to execute at least one of signal input from the piezoelectric element, and signal output to the piezoelectric element;
   a polarization processing unit configured to execute polarization processing in which voltage is applied between the electrodes; and
   a connection switching unit configured to switch between a first connection state with which at least one of the electrodes and the signal processing unit are connected, and a second connection state with which at least one of the electrodes and the polarization processing unit are connected.

10. The piezoelectric sensor device according to claim 9, wherein
    the signal input from the piezoelectric element includes detection processing for detecting an electrical signal output from the piezoelectric element.

11. The piezoelectric sensor device according to claim 10, wherein
    the signal output to the piezoelectric element includes drive processing for outputting a drive signal to the piezoelectric element to drive the piezoelectric element.

12. The piezoelectric sensor device according to claim 9, wherein
    the signal output to the piezoelectric element includes drive processing for outputting a drive signal to the piezoelectric element to drive the piezoelectric element.

13. A piezoelectric sensor device drive method for driving a piezoelectric sensor device including a piezoelectric element having a piezoelectric body and a pair of electrodes sandwiching the piezoelectric body, a signal processing unit configured to execute at least one of signal input from the piezoelectric element, and signal output to the piezoelectric element, a polarization processing unit configured to execute polarization processing in which polarization voltage is applied to the piezoelectric element, and a connection switching unit configured to switch between a first connection state with which the electrodes and the signal processing unit are connected and a second connection state with which the electrodes and the polarization processing unit are connected, the piezoelectric sensor device drive method comprising:
    switching a connection state of the connection switching unit to the second connection state, and applying the polarization voltage to the piezoelectric element using the polarization processing unit; and after the switching of the connection state to the second connection state, switching the connection state of the connection switching unit to the first connection state, and executing the at least one of the detection processing and the signal processing by the signal processing unit.

14. The piezoelectric sensor device method according to claim 13, wherein
the signal input from the piezoelectric element includes detection processing for detecting an electrical signal output from the piezoelectric element.

15. The piezoelectric sensor device method according to claim 14, wherein
the signal output to the piezoelectric element includes drive processing for outputting a drive signal to the piezoelectric element to drive the piezoelectric element.

16. The piezoelectric sensor device method according to claim 13, wherein
the signal output to the piezoelectric element includes drive processing for outputting a drive signal to the piezoelectric element to drive the piezoelectric element.

* * * * *